US007270656B2

(12) United States Patent
Gowda et al.

(10) Patent No.: US 7,270,656 B2
(45) Date of Patent: Sep. 18, 2007

(54) COOLED LASER FIBER FOR IMPROVED THERMAL THERAPY

(75) Inventors: Ashok Gowda, Houston, TX (US); Roger McNichols, Pearland, TX (US); Marc Gelnett, Houston, TX (US); Matthew Fox, Bellaire, TX (US)

(73) Assignee: Visualase, Inc., Houston, TX (US)

( * ) Notice: Subject to any disclaimer, the term of this patent is extended or adjusted under 35 U.S.C. 154(b) by 376 days.

(21) Appl. No.: 10/703,304

(22) Filed: Nov. 7, 2003

(65) Prior Publication Data
US 2006/0217693 A1    Sep. 28, 2006

(51) Int. Cl.
*A61B 18/18*    (2006.01)
(52) U.S. Cl. .............................. 606/15; 606/16; 606/22; 606/167; 607/88
(58) Field of Classification Search .................. 606/7, 606/10, 13–16, 20–23, 167, 170; 607/88, 607/89, 92
See application file for complete search history.

(56) References Cited

U.S. PATENT DOCUMENTS

| | | | |
|---|---|---|---|
| 4,140,130 A | 2/1979 | Storm, III | |
| 4,669,467 A | 6/1987 | Willett et al. | |
| 4,785,815 A | 11/1988 | Cohen | |
| 4,832,024 A | 5/1989 | Boussignac et al. | |
| 4,852,567 A | 8/1989 | Sinofsky | |
| 4,862,887 A | 9/1989 | Weber et al. | |
| 4,959,063 A * | 9/1990 | Kojima | 606/15 |
| 5,061,265 A | 10/1991 | Abela et al. | |
| 5,169,396 A * | 12/1992 | Dowlatshahi et al. | 606/15 |
| 5,246,436 A * | 9/1993 | Rowe | 606/13 |
| 5,303,324 A * | 4/1994 | Lundahl | 385/147 |
| 5,312,392 A | 5/1994 | Hofstetter et al. | |
| 5,330,465 A | 7/1994 | Doiron et al. | |
| 5,348,552 A | 9/1994 | Nakajima et al. | |
| 5,454,807 A | 10/1995 | Lennox et al. | |
| 5,545,161 A | 8/1996 | Imran | |
| 5,607,421 A | 3/1997 | Jeevanandam et al. | |
| 5,792,100 A | 8/1998 | Shantha | |
| 5,824,005 A | 10/1998 | Motamedi et al. | |

(Continued)

FOREIGN PATENT DOCUMENTS

DE    4137983 A1    11/1991

OTHER PUBLICATIONS

Weber et al., "Laser versus Radiofrequency Catheter Ablation of Ventricular Myocardium in Dogs: A Comparative Test," Cardiology, vol. 88, 1997, pp. 346-352.

(Continued)

*Primary Examiner*—A. Farah

(57) ABSTRACT

In one embodiment, the disclosure is directed to an integrated apparatus for delivering energy to a tissue. The integrated apparatus included a housing having a distal end and a tubular structure located within the housing forming a first annulus between the tubular structure and the housing. The tubular structure is configured to accept an energy delivery component and is configured to form a second annulus between the tubular structure and the energy delivery component. The first annulus and the second annulus are configured to communicate with each other proximate to the distal end of the housing.

49 Claims, 11 Drawing Sheets

U.S. PATENT DOCUMENTS

| | | |
|---|---|---|
| 5,830,196 A | 11/1998 | Hicks |
| 5,906,606 A | 5/1999 | Chee et al. |
| 5,997,571 A | 12/1999 | Farr et al. |
| 6,106,514 A | 8/2000 | O'Donnell, Jr. |
| 6,212,426 B1 | 4/2001 | Swanson |
| 6,283,958 B1 * | 9/2001 | Vogl et al. ............... 606/15 |
| 6,383,179 B1 * | 5/2002 | Neuberger ............... 606/16 |
| 6,503,246 B1 * | 1/2003 | Har-Shai et al. ............ 606/23 |
| 6,576,163 B2 * | 6/2003 | Mersch ................. 264/1.1 |

OTHER PUBLICATIONS

Welch et al., "Evaluation of Cooling Techniques for the Protection of the Epidermis During Nd: YAG Laser Irradiation of the Skin," in Neodymium-YAG Laser in Medicine and Surgery, S.N. Joffe, Ed. New York: Elsevier, 1983, pp. 196-204.

U.S. Appl. No. 10/208,222, filed Jul. 30, 2002 entitled "Cooled Tip Laser Catheter for Sensing and Ablation of Cardiac Arrhythmias,".

* cited by examiner

TO ENERGY SOURCE

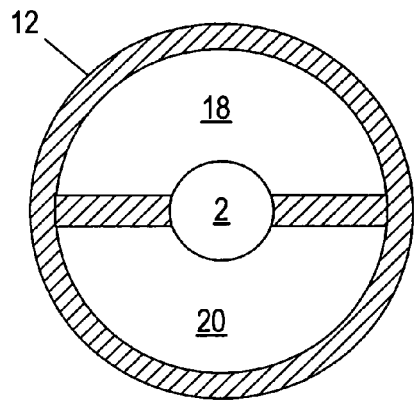
*FIG. 4G*
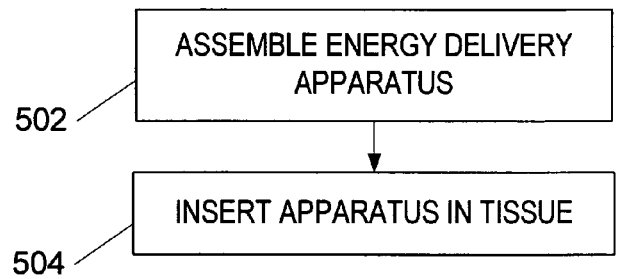
*FIG. 5*
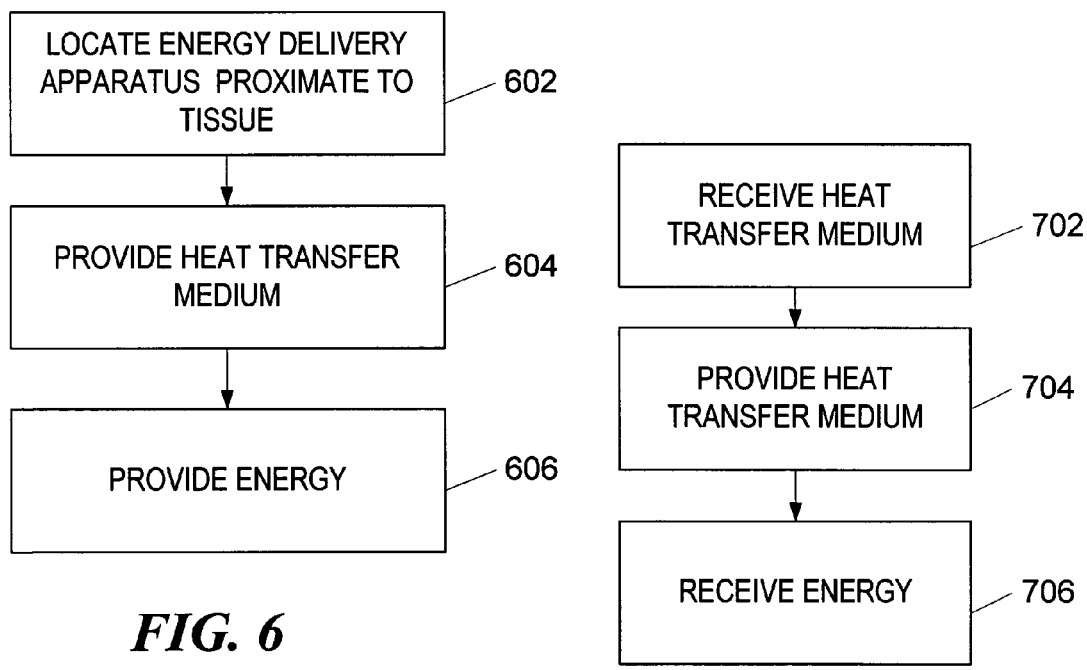
*FIG. 6*
*FIG. 7*

COOLED LASER FIBER FOR IMPROVED THERMAL THERAPY

FIELD OF THE DISCLOSURE

This disclosure, in general, relates to energy delivery apparatuses, energy delivery systems, and methods for using same.

BACKGROUND

Laser interstitial thermal therapy (LITT) is a clinical tool for treating various malignant tumors in the liver, brain, ENT, or abdominal locations, as well as for treating benign alterations such as prostate adenomas. Fiber optics that terminate in either bare fibers or diffusing applicators are punctured into the pathological volume to deliver the laser energy within the desired region of treatment. After positioning of the fibers, target tissues are irradiated causing volumetric heating that leads to thermal tissue necrosis. Tumor destruction with direct heating is therefore possible, while greatly limiting side effects or additional damage to surrounding structures. Furthermore, such thermal methods are associated with faster recovery than conventional surgical resection procedures.

Large applicators may cause trauma to healthy tissue when accessing the pathological volume. Applicators where light distribution results in high power density and heat generation, exceeding the thermal diffusion into the tissue can cause areas close to the applicator to char and potentially vaporize. Charring limits heat deposition within deeper tissue volumes due to increased absorption of light energy. As charred tissue continues to absorb incident light, its temperature continues to rise, leading to carbonization around the applicator. Further coagulation of deeper layers is dependent on heat conduction away from this carbonized volume.

While it is indeed possible to create large thermal lesions in this manner, the morphology of the resulting lesion is undesirable. Furthermore, high temperatures associated with the carbonized tissue often result in failure of the applicator tip and fiber optic with significant attendant risk for patients. As such, an applicator that limits charring and vaporization would be desirable.

Typical applicators are multi-component applicators. Procedures utilizing these applicators involve multiple insertion steps and time consuming actions taken by the medical professional performing the procedure. Such steps and actions prolong the surgical process and endanger the patient. In addition, multiple insertion steps potentially cause slippage of catheters and additional damage to surrounding tissue. As such, applicators that reduces the number of steps and actions performed by a medical professional would be desirable.

BRIEF DESCRIPTION OF THE DRAWINGS

FIG. 4A–4G are cross sectional views depicting alternate embodiments of a distal section of the energy delivery apparatus.

FIGS. 5–7 are flow diagrams depicting exemplary methods for use of the apparatus.

DETAILED DESCRIPTION

Energy delivery systems, such as Cooled Laser Fiber (CLF) systems, may be used to treat tissue within a patient. For example, a CLF system may be used to treat diseased tissues such as malignant and benign tumors and adenomas. In one exemplary embodiment, an energy delivery apparatus is inserted into the tissue, laser energy is dispersed within the tissue, and as a result, thermal necrosis occurs. The CLF system may be utilized to facilitate thermal coagulation of tissue, and more particularly to treat solid cancerous tumors in soft tissue, such as human and animal tissue.

Figure 1A:
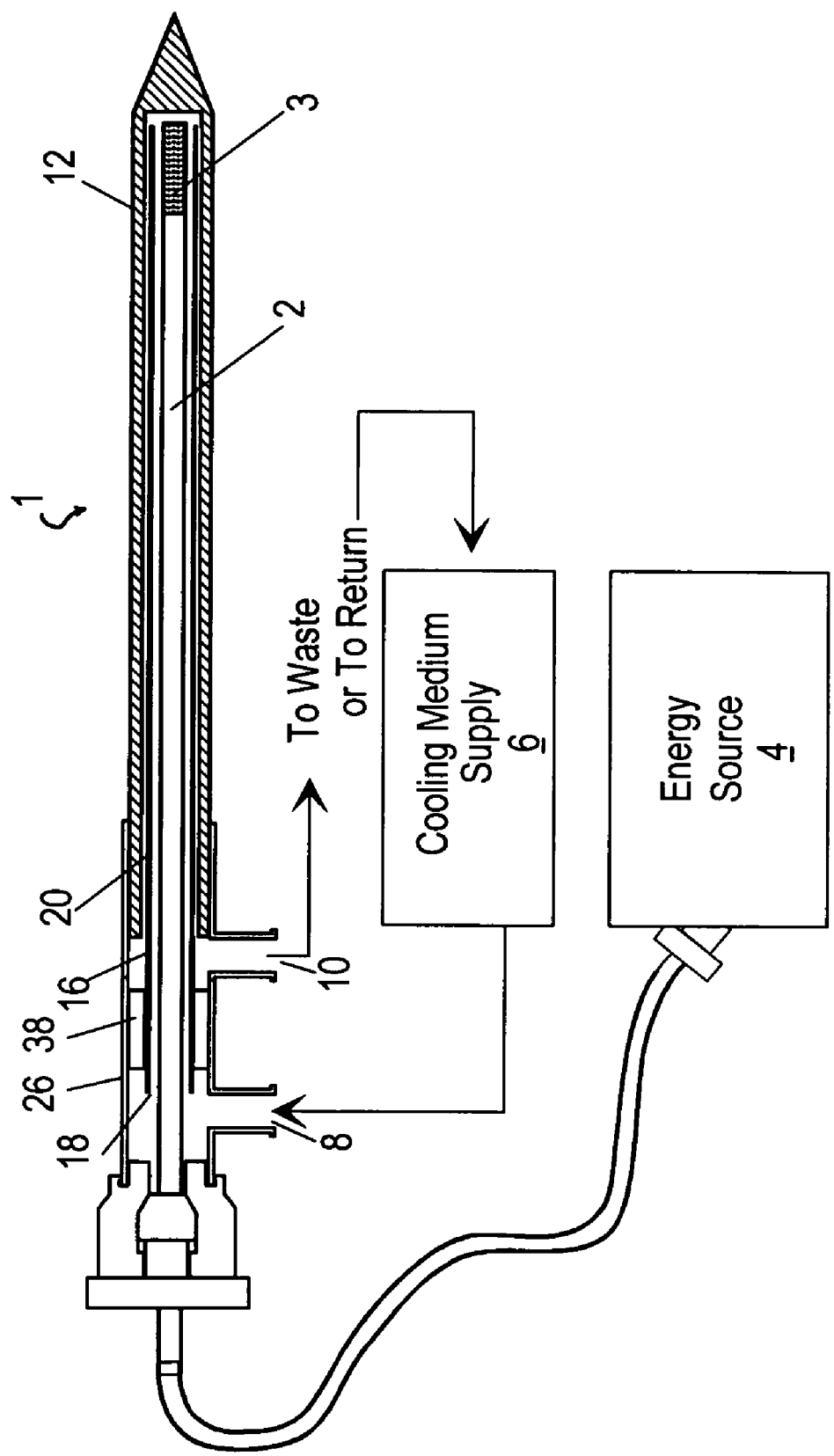
FIG. 1A is a block diagram and plan view of an exemplary energy delivery apparatus in accordance with an embodiment of the disclosures made herein.
Figure 1B:
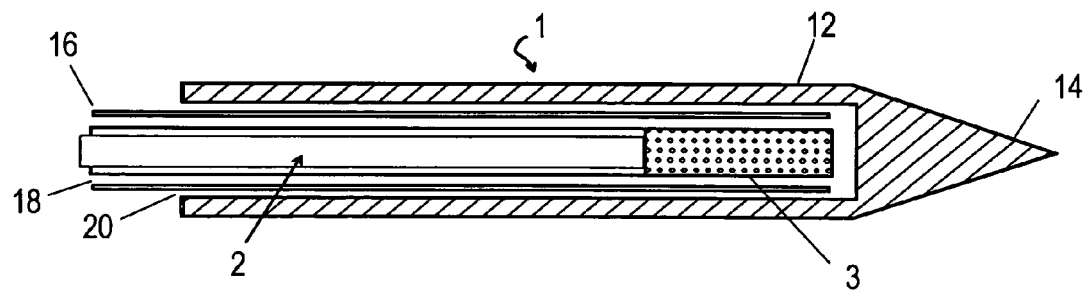
FIG. 1B is a partial fragmentary side view depicting an embodiment of a distal portion of the energy delivery apparatus depicted in FIG. 1A.

FIGS. 1A–1I depict embodiments of exemplary energy delivery apparatuses for used in a Cooled Laser Fiber (CLF) system. As shown in FIG. 1A, the CLF system includes an energy delivery apparatus 1, an energy delivery component 2, an energy source 4, and a cooling media supply apparatus 6. The proximal end of the energy delivery component 2, is coupled to the output of the energy source 4. The distal end 3 of the energy delivery component 2, extends within the energy delivery apparatus 1. The cooling medium supply apparatus 6 is connected to the inlet fluid port 8 of the energy delivery apparatus 1. The outlet fluid port 10 is either connected back to the cooling medium supply apparatus 6 (recirculating system) or to a suitable waste collection area (non-recirculating system).

In the exemplary embodiment depicted, the energy delivery apparatus 1 includes a housing 12 attached to a coupling assembly 26. A structure 16 separates the lumen of housing 12 into two channels. A first channel 20 is formed between the structure 16 and the housing 12 and a second channel 18 is formed between the energy delivery component 2 and the structure 16. The channels 18 and 20 communicate near or proximate the distal end of the housing 12 to allow fluid to pass from one channel to the other. The channels 18 and 20 may be isolated proximate the coupling assembly to allow fluid to, for example, enter port 8, flow through channel 18, return through channel 20, and exit via the outlet port 10. However, in other embodiments, the fluid may flow in the opposite direction. In this manner, counter current cooling fluid flow cools the housing 12, the structure 16, the energy delivery component 2, and the surrounding tissue. In the above exemplary embodiment, the structure 16 is depicted as tubular and the channels 18 and 20 are depicted as annuluses or concentric flow paths. However, various shaped structures 16 or shaped housings 12 may be used to form channels. As such, the tube-like structures, 12 and 16, may have cross-sectional shapes such as stars, squares, triangles, ovals, circles, and other shapes.

In one exemplary embodiment, the energy delivery apparatus 1 and the energy delivery component 2 are integrated or assembled just prior to insertion into the tissue. In another exemplary embodiment, the energy delivery apparatus 1 and the energy delivery component 2 are integrated or assembled during manufacture prior to being delivered for use.

Referring to FIGS. 1B through 1E, energy delivery apparatus 1 includes a flexible outer housing 12 having a tubular structure along its length and a penetrating tip 14 at its distal end. The outer housing 12 may, for example, be rigid enough to penetrate soft tissue without kinking, yet be flexible enough to follow curved or arcuate paths. The solid penetrating tip 14 may take the form of cutting edges or a point, among others. The housing 12 contains an inner tubular structure 16 within its lumen that extends between a proximal end and a distal end of the outer housing 12. The inner tubular structure 16 may be centered within the housing 12 to create fluid inlet lumen 18, and fluid outlet lumen 20. The inlet and outlet lumens facilitate delivery and return of cooling media (e.g. water, saline, or carbon dioxide, among others) to and from the distal end of the energy delivery apparatus 1. The fluid inlet lumen 18 facilitates housing of the energy delivery component 2. Suitable materials for the flexible outer housing 12, and inner tubular structure 16 include, but are not limited to, flexible radio-opaque and non radio-opaque medical grade plastic tubing such as polycarbonate (Makrolon, Bayer Polymers), polyurethane, polyethylene, polypropylene, silicone, nylon, PVC, PET, PTFE, ABS, PES, PEEK, FEP, and other biocompatible polymers.

In one particular embodiment, the inner diameter of the inner tubular structure 16 may range from 0.6 mm to 2.0 mm, such as between 0.9 mm and 1.1 mm. The outer diameter of the inner tubular structure 16 may range from 0.7 mm to 2.1 mm, such as between 1.0 mm to 1.2 mm. The inner diameter of the outer housing may range from 1.0 mm to 1.9 mm, such as between 1.2 mm and 1.4 mm, and the outer diameter of the outer housing may range from 1.2 mm to 2.5 mm, such as between 1.3 mm and 1.6 mm or less than 1.5 mm. For example, in a preferred embodiment in which a 0.4 mm core diameter fiber optic is used as the energy delivery component, and which is further provided with a buffer jacket of 0.730 mm outer diameter (OD), the inner tubular structure 16 is preferably 1.09 mm ID and 1.17 mm OD, and the outer housing is preferably 1.37 mm ID and 1.57 mm OD. Prefabrication or integration permits smaller diameters, which cause less peripheral tissue damage and may be easier to guide through tissue.

The energy delivery component 2 disposed within the fluid inlet lumen includes one or more optical waveguides positioned to direct light through both the inner tubular structure 16 and outer housing 12. In a particular embodiment, the energy delivery component 2 may be movable relative to the energy delivery apparatus 1, for example, translating along the axis of the energy delivery apparatus 1. Energy emitted from a diffusing tip of the energy delivery component 2 may pass through transparent housing 12 and structure 16. More than one region of tissue located along the housing 12 may be treated by moving the energy delivery component 2.

Figure 1C:
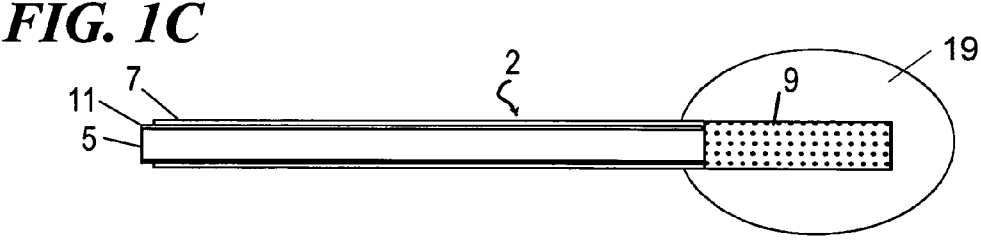
FIG. 1C is a partial fragmentary side view depicting an embodiment wherein the energy delivery component includes a diffusing tip element.
Figure 1D:
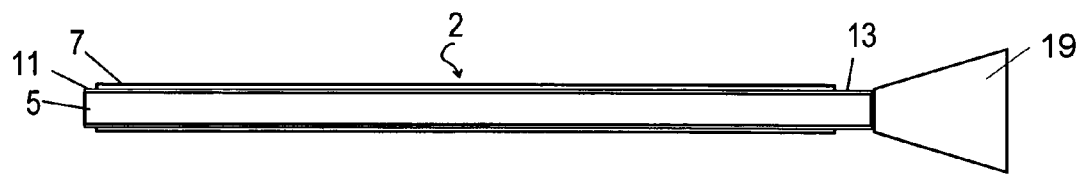
FIG. 1D is a partial fragmentary side view depicting an embodiment wherein the energy delivery component has a bare tip optical waveguide.
Figure 1E:
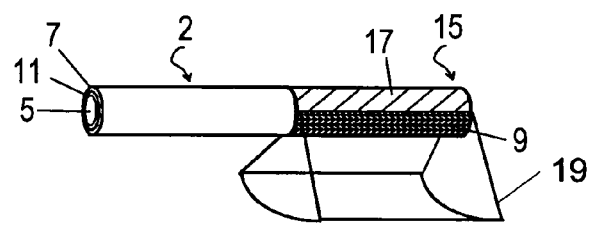
FIG. 1E is a partial fragmentary side view depicting an embodiment wherein the energy delivery component includes a diffusing tip element with reflective means for selective angular energy emission.

In at least one embodiment, the distal end 3 of the energy delivery component 2 preferably consists of an optical waveguide terminated with a diffusing tip element 9, as shown in FIG. 1C. The diffusing tip element 9 is designed to emit light 19 in a uniform cylindrical pattern around the center axis of the waveguide. In at least one embodiment, the waveguide is an optical fiber with core 5, cladding 11, and protective jacket 7. In an alternate embodiment shown in FIG. 1D, energy delivery component 2 may consist of a bare tipped optical waveguide in which the distal end of the optical waveguide is polished flat resulting in a forward propagation of emitted energy 19. In yet another alternate embodiment, energy delivery component 2 may consist of an optical waveguide terminated with a selective angular emitting element 15, as shown in FIG. 1E. The angular emitting element 15 may be constructed by placing a reflective material 17 over a section of a diffusing tip element 9 thereby preventing significant energy from passing through that section of the element. Suitable materials for the reflective material 17 include polished surfaces of gold, silver, aluminum, and other reflective materials. In one exemplary embodiment, the energy delivery component 2 may be rotated to direct photons 19 emitted from the angular emitting element 15.

Figure 1F:
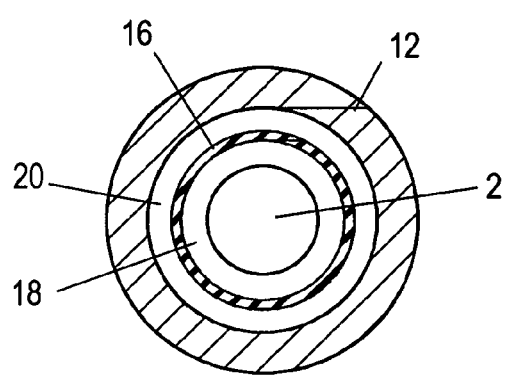
FIG. 1F is a cross sectional view depicting an embodiment of a distal section of the energy delivery apparatus.

A cross section of a distal portion of an energy delivery apparatus 1 is shown in FIG. 1F. In at least one embodiment, the fluid inlet lumen 18 is defined by the space between the energy delivery component 2 and the inner wall of the inner tubular structure 16. The fluid outlet lumen 20 is defined by the space between the outer wall of the inner tubular structure 16 and the inner wall of the outer tubular housing 12. In alternate embodiments, the cross-sectional shape of the energy delivery apparatus may take forms such as a circle, triangle, star-shape, and oval, among others. In further embodiments, the outer housing may be shaped to form separate channels. In another exemplary embodiment, the structure 16 may be corrugated to provide channels. The outer surface of housing 12 may be shaped to increase heat transfer surface area.

Figure 1G:
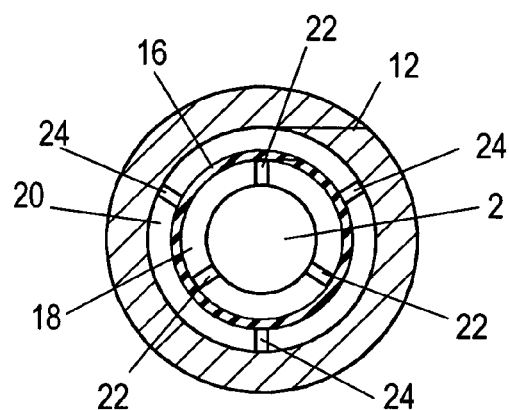
FIG. 1G is a cross sectional view depicting an alternate embodiment of a distal section of the energy delivery apparatus with means for maintaining consistent lumen dimensions during use.

A cross section of an alternate embodiment of the energy delivery apparatus 1 is shown in FIG. 1G. In one embodiment, energy delivery apparatus 1 may include one or more inner spacers 22 located between inner tubular structure 16 and energy delivery component 2 and one or more outer spacers 24 located between inner tubular structure 16 and outer tubular housing 12. The inner spacers 22 may maintain a consistent distance between energy delivery component 2 and inner tubular structure 16 around the circumference of energy delivery component 2 such as to maintain consistent lumens or to limit movement of one lumen with respect to the other. Similarly, the purpose of outer spacers 24 is to maintain a consistent distance between inner tubular structure 16, and outer tubular housing 12 around the circumference of inner tubular structure 16. It should be noted that inner spacers 22 and outer spacers 24 may extend along the entire length of energy delivery apparatus 1 or alternatively may only be located along discrete sections where maintaining consistent profiles may be more important such as near the distal end 3 of energy delivery component 2. In alternate embodiments, the structure 16 or the housing 12 may be shaped to form channels or provide structural integrity for maintaining open lumens.

Figure 1H:
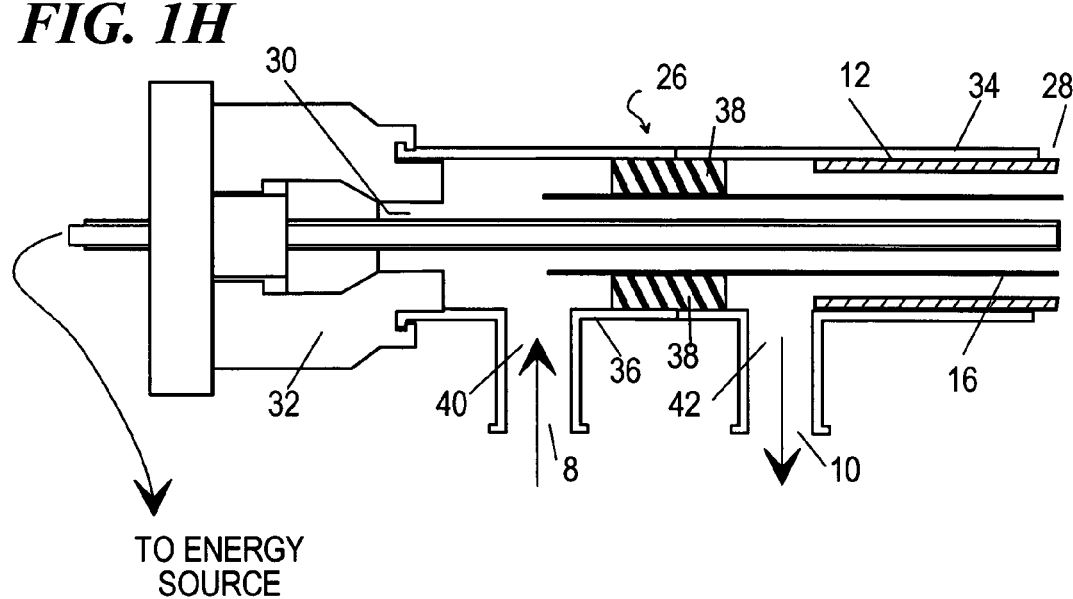
FIGS. 1H and 1I are partial fragmentary side views depicting embodiments of proximal portions of the energy delivery apparatus depicted in FIG. 1A.
Figure 1I:
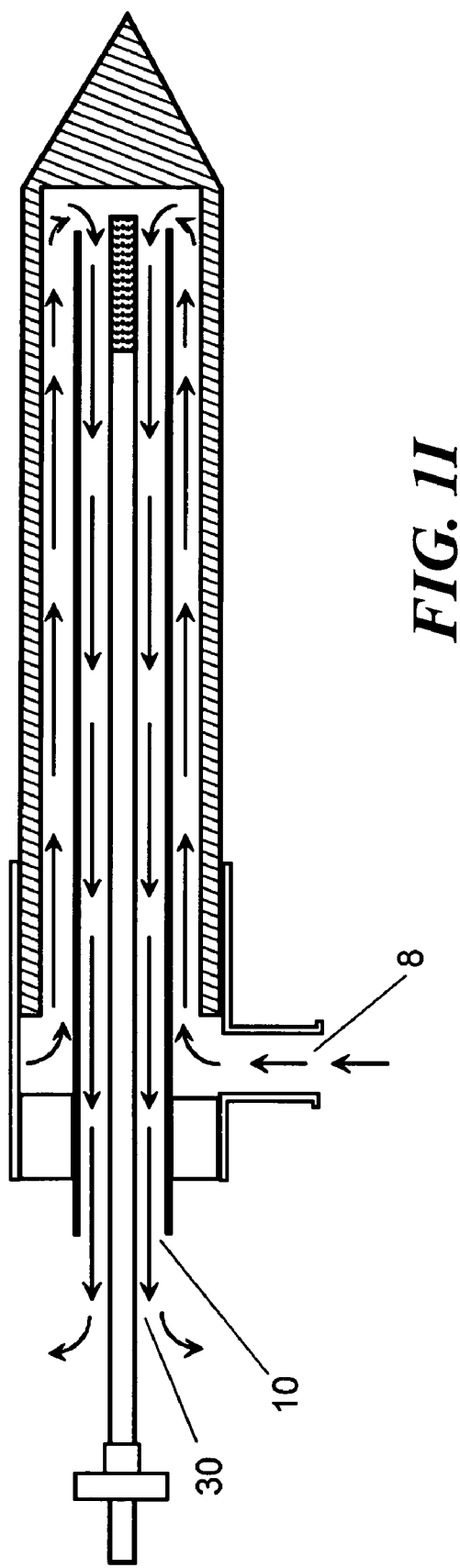

Referring to FIG. 1H, a coupling assembly 26 is attached at the proximal end 28 of the outer housing 12. The coupling assembly 26 includes the inlet fluid port 8, outlet fluid port 10 and an opening 30 for introducing an energy delivery component 2. A suitable coupling assembly may be formed by mating two male-female taper luer tees, such as part# LT878-9, Value Plastics, Inc. A male Touhy Borst connector 32, such as part# 80344 Qosina, may be included to provide a leak-proof seal at the energy delivery component opening 30 and for securing the energy delivery component 2 to the coupling assembly 26. The distal segment 34 of the coupling assembly is bonded to the outer housing 12 to create a fluid tight seal. A proximal section 36 of coupling assembly 26 contains a seal 38 between the inner tubular structure 16 and the proximal section 36 to prevent fluid communication between inlet fluid port 8 and outlet fluid port 10 within the coupling assembly 26. Both distal and proximal seals and other bonds may be created using a suitable UV cure epoxy, such as Part# 140-M, Dymax Corp. Alternative methods of bonding and sealing may be used including various cyanoacrylates, epoxies, silicones, heat bonds, press fits, and threaded assemblies, among other methods. It is contemplated that the opening 30 and one of inlet fluid port 8 or outlet fluid port 10 may be coincident. FIG. 1I portrays a schematic of an integrated energy delivery apparatus wherein fluid outlet port 10 and energy delivery component opening 30 mutually comprise one another.

A heat transfer medium supply passage 40 extends between the inlet fluid port 8 and the fluid inlet lumens 18 for enabling flow of heat transfer medium from a heat transfer medium supply apparatus 6 through the coupling assembly 26 into the fluid inlet lumen 18. A heat transfer medium return passage 42 extends between the fluid outlet port 10 and fluid outlet lumen 20 for enabling flow of heat transfer medium from the fluid outlet lumen 20 through the coupling assembly 26 and out of the energy delivery apparatus 1. The heat transfer medium may, for example, be a cooled medium, a heated medium, or a medium having a temperature different than that of the tissue, such as a room-temperature medium.

An embodiment of a heat transfer medium supply apparatus may be a circulation type medium supply apparatus or a non-circulation type medium supply apparatus. In a circulation type medium supply apparatus, heat transfer medium is supplied from a reservoir to the energy delivery apparatus 1 and back to the reservoir. In a non-circulation type medium supply apparatus, heat transfer medium is supplied from a supply reservoir to the energy delivery apparatus 1 and then to a separate return reservoir. An example of a non-circulation type medium apparatus system includes a syringe pump, wherein a body of a syringe is a supply reservoir. Benefits of the use of a syringe pump include ease of metering the heat transfer medium and reduced potential for contamination of heat transfer medium being supplied to the circulation chamber. Suitable syringe pumps are commercially available from New Era Pump Systems Corporation and from Harvard Apparatus Corporation.

Figure 2A:
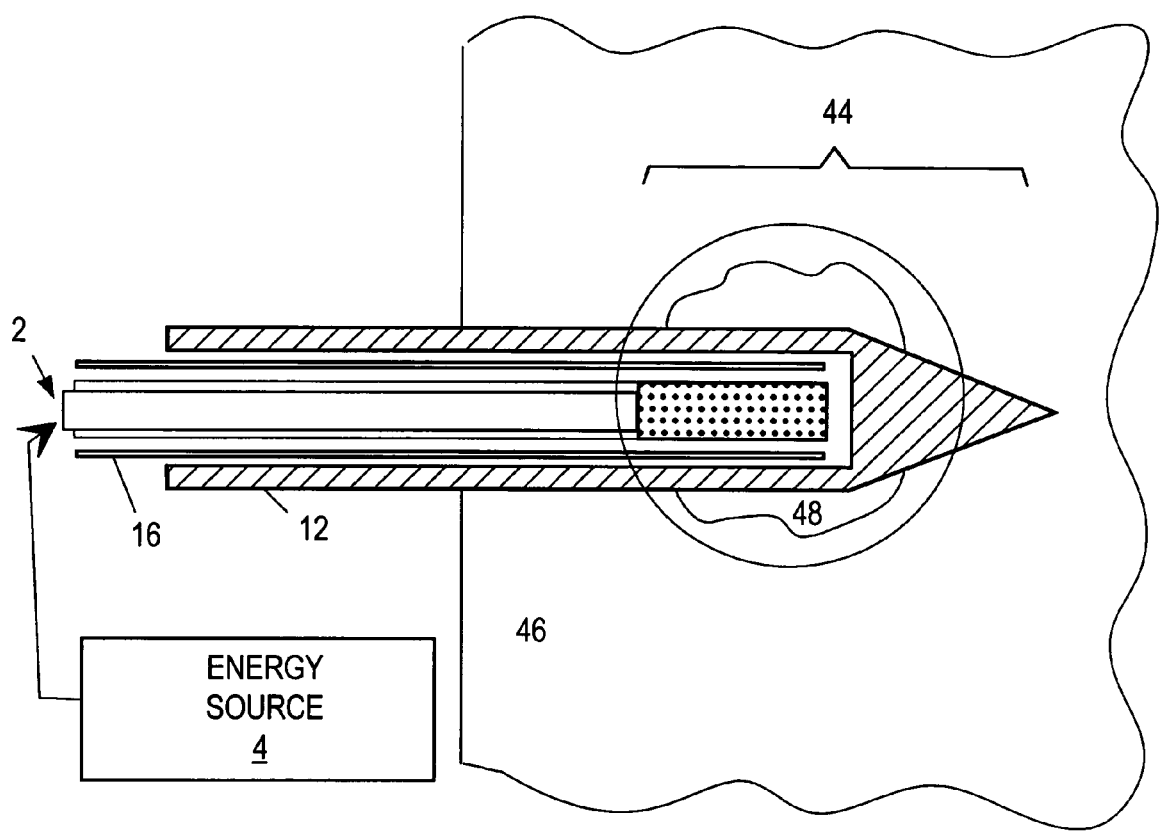
FIG. 2A is a diagrammatic view depicting an embodiment of a method of treatment with an energy delivery apparatus of a Cooled Laser Fiber (CLF) system.

FIG. 2A depicts an embodiment of a method for utilizing the energy delivery apparatus 1 depicted in FIG. 1A through 1E. The distal portion 44 of the energy delivery apparatus 1 is inserted into the tissue 46 of a patient and directly within the diseased tissue 48. The distal portion 44 may be guided into the tissue 46 via a percutaneous approach under a known guidance approach such as fluoroscopic, MRI, ultrasound, CT, stereotaxis, among others. In one exemplary embodiment, the energy delivery apparatus is inserted through a guide hole or incision. In another exemplary embodiment, the energy delivery apparatus may be inserted directly into tissue without an introducer or catheter. Once at a location to be treated, such as within the diseased tissue, energy is delivered into the diseased tissue after passing from an energy source 4, through the energy delivery apparatus 2, through the medium within the fluid inlet lumen 18, through the inner tubular structure 16, through the medium within the fluid outlet lumen 20, and through the outer housing 12. In one embodiment, the energy source 4 is a laser operating at a wavelength between 350 nm and 2100 nm, such as at about 980 nm.

During delivery of energy, a cooling medium is introduced into the energy delivery apparatus 1 such that it flows through the fluid inlet lumen 18 around and in contact with the energy delivery component 2. The cooling medium exits the fluid inlet lumen 18 at the distal end of the inner tubular structure 16 and enters the fluid outlet lumen 20 at the distal end of the outer housing 12. The cooling medium flows back through the energy delivery apparatus 1 and exits the fluid outlet lumen 20 at the proximal end of the outer housing 12. During this travel the cooling medium contacts the inner tubular structure 16, the energy delivery component 2 and the outer housing 12, thus cooling the inner tubular structure 16, the energy delivery component 2, the outer tubular housing 12, and tissue 46 in contact with the energy delivery apparatus 1. Accordingly, both the tissue under treatment and the energy delivery apparatus 1 are cooled, minimizing the possibility of damaging energy delivery component 2 and energy delivery apparatus 1, or overheating adjacent tissue. It should be appreciated that the direction of flow could be reversed with the inlet flow traveling between the outer housing 12 and inner tubular structure 16 and the outlet flow traveling through the lumen of the inner tubular structure 16. In either method of operation, both the energy delivery component 2, and tissue 46 in contact with energy delivery apparatus 1 will experience cooling.

The temperature and/or flow rate of the cooling medium may be controlled to provide a desired cooling of tissue or energy delivery component. It is contemplated herein that the cooling medium may flow in a continuous or in an intermittent manner. Modulating supply temperature and/or flow rate of the cooling medium allows for increased deposition of photon energy by reducing or eliminating damage of tissue in direct contact with energy delivery apparatus 1, thus leading to development of increased possible lesions sizes.

The heat transfer medium may be a cooling medium or a heating medium. Examples of the cooling medium include room temperature and chilled fluids including liquids and gases such as saline solution, water, air, nitrogen, carbon dioxide, alcohols, and other suitable substances. Suitable substances include fluids with a suitable heat capacity and/or that are transmissive to the wavelength of light emitted from the energy delivery component 2. In some embodiments, the fluid may also include sealants, coagulants, anti-coagulants, anesthetics, optical agents, radio-opaque agents, dyes, magnetic resonance agents, therapeutic drugs, and chemotherapy agents, among other treatment agents.

In one exemplary embodiment, a fluid containing an MRI contrast agent may be used during insertion of the energy delivery apparatus 1. The cooling fluid may be optionally changed during energy delivery or therapeutic agents may be added at appropriate times during treatment.

It is contemplated herein that before, during and/or after the delivery of energy, induced temperatures may be monitored using MRI-based thermometry. Accordingly, procedures may be conducted for facilitating estimation of thermal damage at the active area of the energy delivery apparatus 1 and furthermore for preventing overheating of energy delivery apparatus 1, or other tissues in its surrounding area.

Cooling tissue in accordance with embodiments of the disclosures made herein permits creation of larger thermal lesions in a safer manner. Cooling of the tissue in contact with energy delivery apparatus 1 limits such tissue from being charred or carbonized by overheating. By limiting the formation of carbonized tissue, forward propagation of photons by direct absorption is not impeded, thus allowing continued lesion growth from volumetric heating by deeper penetration of photons prior to absorption, as opposed to primarily conductive heating as in the case of carbonized tissue. Furthermore, there is a reduced potential for the energy delivery component 2 to overheat and cause damage or destruction of components comprising the energy delivery apparatus 1. Furthermore, cooling tissue near the interface of energy delivery apparatus, where power density and/or induced temperature is highest, means that energy may be deposited at a higher rate or in greater quantity without reaching undesirable temperature elevation in tissue.

In one exemplary embodiment, energy may be applied at a rate of 8 to 9 watts for a period of 3 to 5 minutes. Lesions of greater than 2 cm diameter may be created quickly in less than 1 minute of treatment, improving the likelihood and efficiency of complete treatment of cancerous lesions or other tissues. Cooling methods in accordance with the disclosures maintain energy delivery apparatuses, such as laser applicators, below threshold temperatures for thermal destruction and providing removal of surface heat, allowing deeper and longer lasting penetration of photons in treated tissue.

Figure 2B:
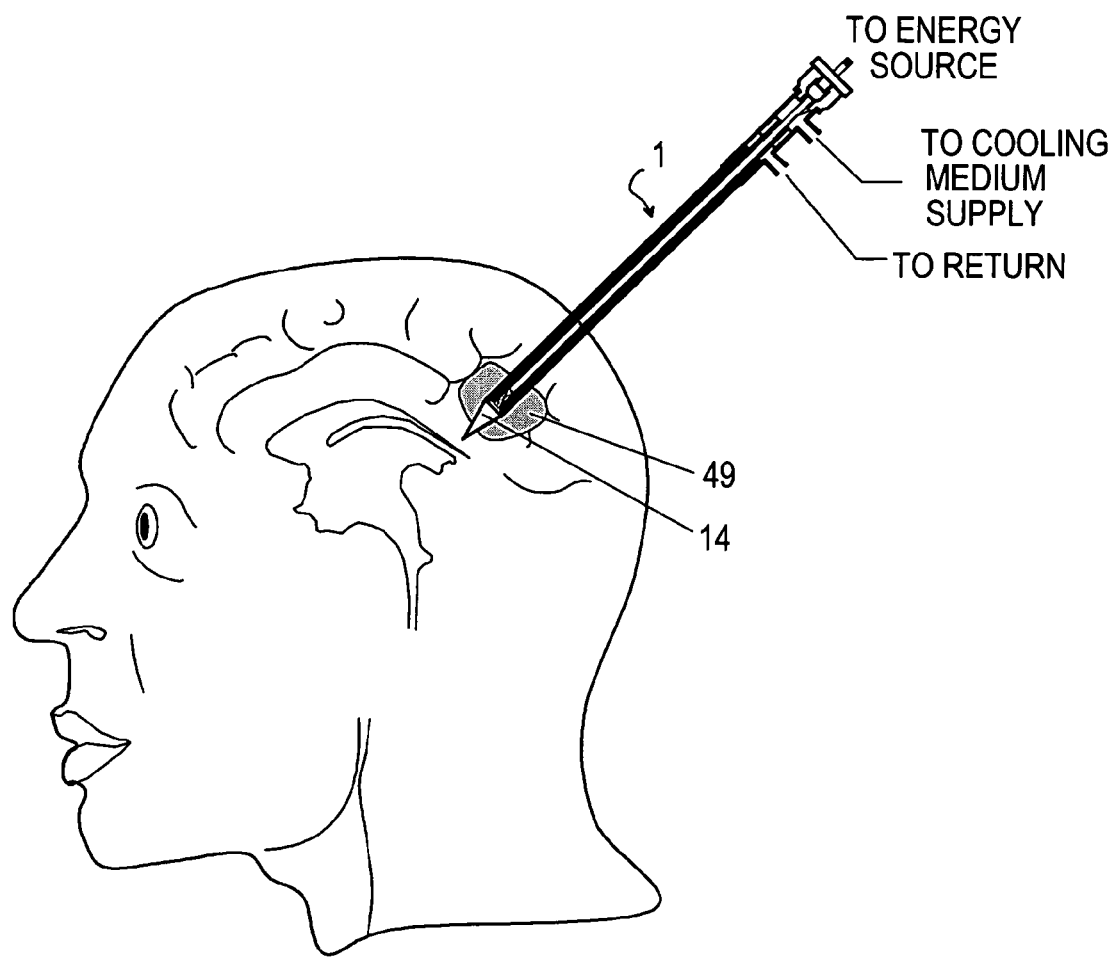
FIG. 2B is a diagrammatic view depicting an exemplary embodiment of a method of treatment with an energy delivery apparatus of a CLF system.

FIG. 2B depicts one exemplary application for the CLF apparatus. In this exemplary application, the apparatus is inserted through healthy tissue such as brain tissue and into a tumor 49. The distal end of the energy delivery component is located within the tumor 49 and energy is transmitted to the diseased tissue. The cooling medium cools the energy delivery apparatus and tissue in contact with the energy delivery apparatus. Alternate embodiments may also permit delivery of therapeutic agents to the diseased tissue.

Figure 3A:
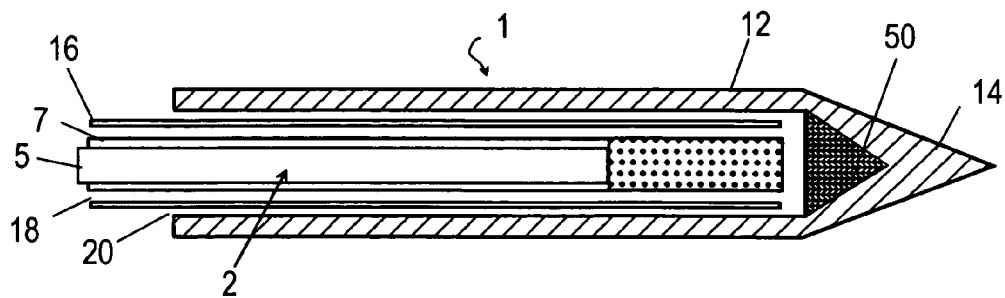
FIG. 3A is a partial fragmentary side view depicting an embodiment of a distal portion of the energy delivery apparatus depicted in FIG. 1A having embedded scattering centers in the distal tip.

FIG. 3A depicts an alternate embodiment of the energy delivery apparatus 1 wherein the penetrating tip portion 14 of the outer housing 12 includes a region of light scattering particles 50 embedded within the tip for preventing excessive forward propagation of light from energy delivery component 2. The region of light scattering is adapted to allow increased power use while preventing high power densities at the distal end of the energy delivery apparatus 1 and can also be used to tailor the shape of the resulting lesion.

Figure 3B:
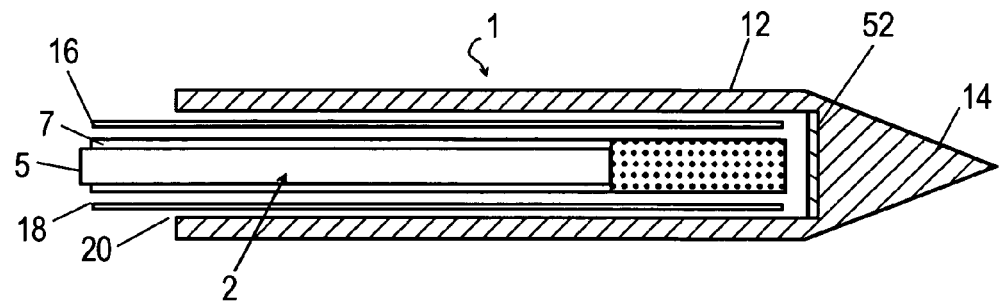
FIG. 3B is a partial fragmentary side view depicting an embodiment of a distal portion of the energy delivery apparatus depicted in FIG. 1A having reflective means at the distal tip.

FIG. 3B depicts an alternate embodiment of the energy delivery apparatus 1 wherein a reflective component 52 is included within the distal end of the outer housing 12. The reflective component 52 prevents significant forward propagation and increases photon scattering along the length of the laser delivery component 2 by causing photons which exit the distal end of laser delivery component 2 to be reflected back into the diffusing tip element 3 where their chances for being scattered out along the length of diffusing tip element 3 and into the tissue increase. Use of reflective component 52 may also aid in tailoring the resulting energy distribution emitted along the length of energy delivery apparatus 1 and hence the resulting lesion within the tissue.

Figure 3C:
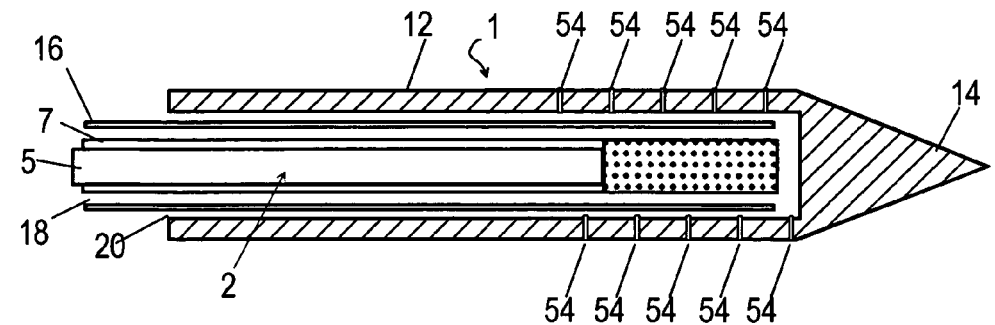
FIG. 3C is a partial fragmentary side view depicting an embodiment of a distal portion of the energy delivery apparatus depicted in FIG. 1A with means for perfusing tissue adjacent to the energy delivery apparatus.

FIG. 3C depicts an alternate embodiment of the energy delivery apparatus 1 wherein the outer housing 12 includes perforations 54 along its length. Perforations 54 may provide increased tissue cooling, or alternatively may be used for administration of anesthetics, therapeutic drugs, light absorptive agents, agents that alter the optical properties of the tissue or other fluids. Alternately, membranes may be incorporated into the housing to allow agents to pass into the tissue. In alternate embodiments, fluid may be extracted from the tissue for testing purposes.

Figure 3D:
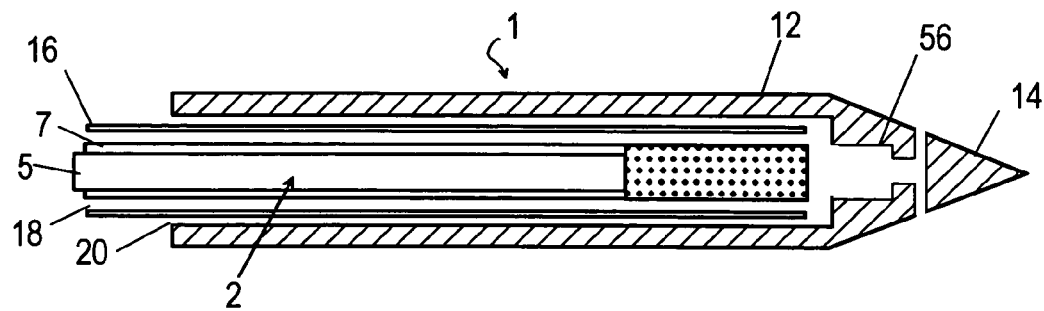
FIG. 3D is a partial fragmentary side view depicting an embodiment of a distal portion of the energy delivery apparatus depicted in FIG. 1A that allows infusion of fluids through the distal tip by retraction of the diffusing tip optical waveguide

FIG. 3D depicts an alternate embodiment of the energy delivery apparatus 1 wherein the penetrating tip 14 of the outer housing 12 is modified to include one of more distal fluid pathways 56. The fluid pathway 56 may be optionally opened or closed by retracting or advancing the energy delivery component 2. The tip of the energy delivery component 2 is designed such that it seals the opening of the distal fluid pathway when advanced into the fluid pathway.

Figure 3E:
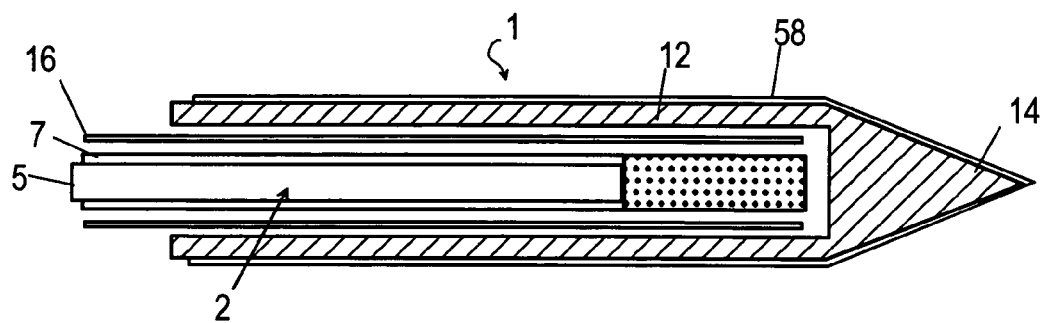
FIG. 3E is a partial fragmentary side view depicting an embodiment of a distal portion of the energy delivery apparatus depicted in FIG. 1A having an optically transmissive coating that provides a non-stick surface.

FIG. 3E depicts an alternate embodiment of the energy delivery apparatus 1 wherein the outer housing 12 is provided with a thin non-stick coating 58. The coating 58 may include one of a number of fluoropolymers or silicones with high temperature handling capability and non-stick surface properties with respect to thermally coagulated tissues. Materials for outer housing 12 can then be chosen based on the desired stiffness of the energy delivery apparatus 1 while the thin coating 58 of fluoropolymer or silicone provides the ideal surface properties.

Figure 3F:
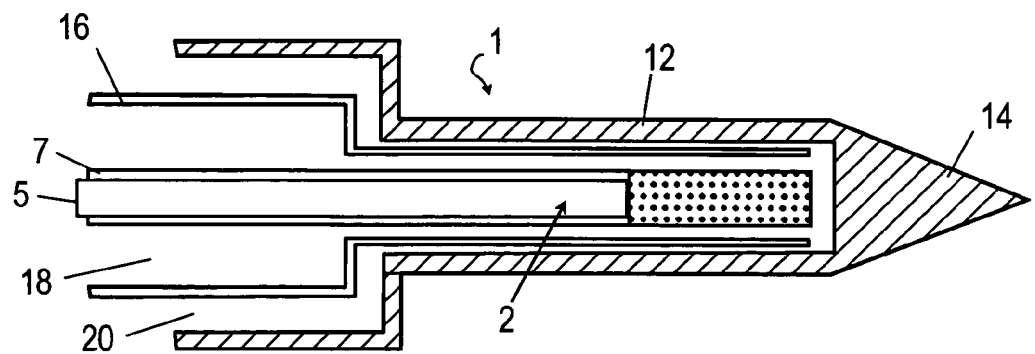
FIG. 3F is a partial fragmentary side view depicting an embodiment of a distal portion of the energy delivery apparatus depicted in FIG. 1A having a stepped down diameter at the distal end of the energy delivery apparatus.
Figure 3G:
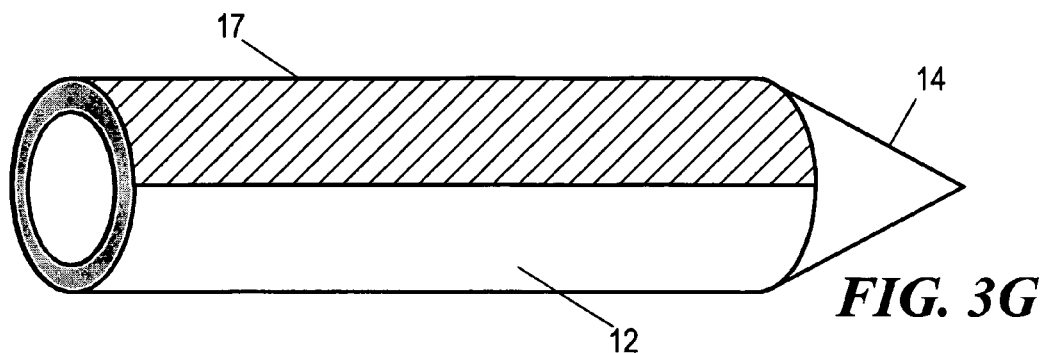
FIGS. 3G–3J are partial fragmentary isometric views depicting embodiments of outer housing and tubular structures of energy delivery apparatus depicted in FIG. 1A with reflective materials used for selective angular energy emission.
Figure 3H:
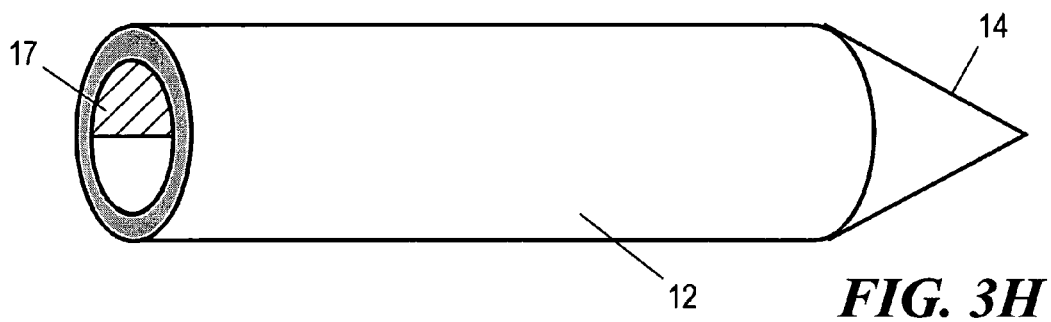
Figure 3I:
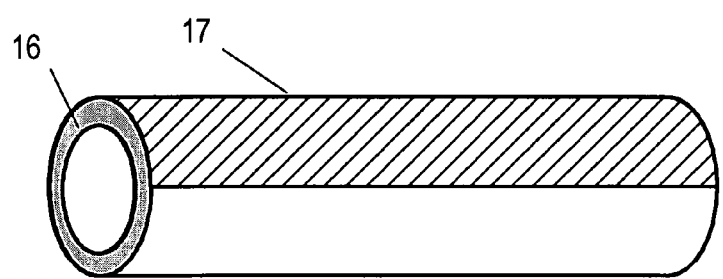
Figure 3J:
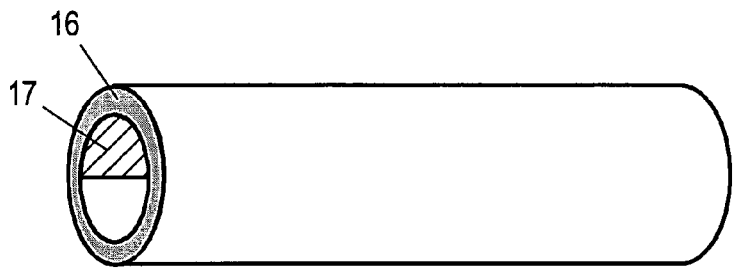

FIG. 3F depicts an alternative embodiment of the energy delivery apparatus 1 wherein the outer housing 12 and inner tubular structure 16 are constructed with a stepped down diameter at the distal end of the energy delivery apparatus 1. Accordingly the resistance to flow of the cooling media can be significantly reduced by shortening the length of the energy delivery apparatus that consists of smaller lumen areas for fluid flow. By doing so a significantly smaller diameter for outer housing 12 at the active site for laser delivery can be created allowing penetration into tissues with less force and with less trauma to surrounding normal tissues.

FIGS. 3G–3J depict alternative embodiments in which reflective material 17 is placed around a semi circular section of the outer or inner surface of either the outer housing 12 or inner tubular structure 16. Any single or combination of the embodiments depicted may be used to preferentially emit energy over an angular region of energy delivery apparatus 1.

Figure 4A:
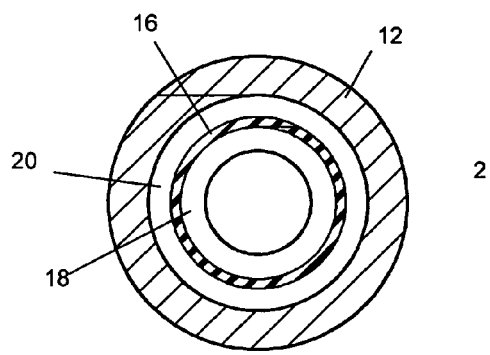
Figure 4B:
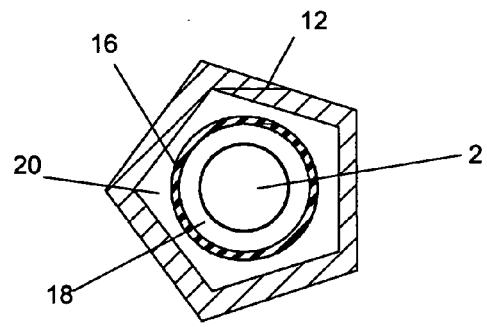
Figure 4C:
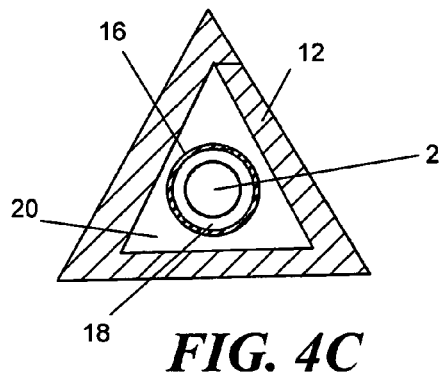
Figure 4D:
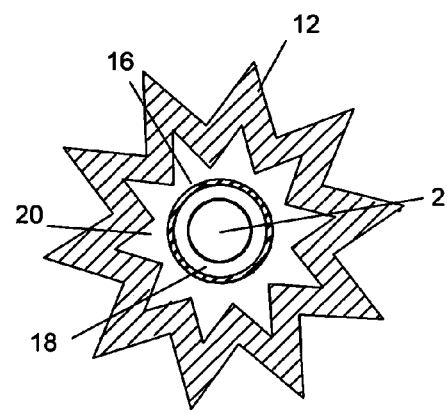
Figure 4E:
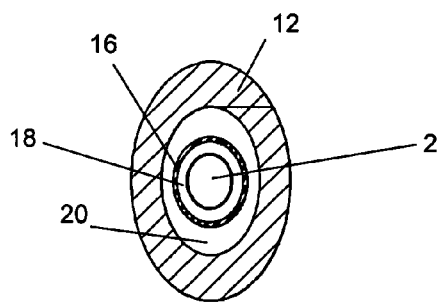
Figure 4F:
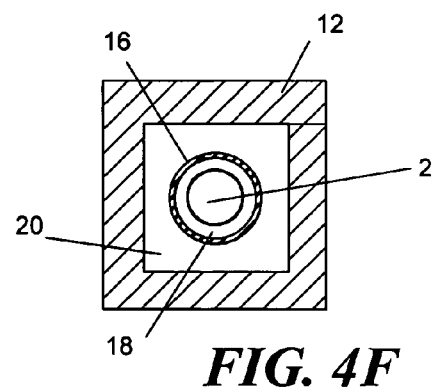

FIGS. 4A–4F depict cross-sections of exemplary embodiments of integrated energy apparatuses. FIG. 4A depicts a cross-section of an exemplary embodiment in which the energy delivery component 2, the structure 16, and the housing 12 form concentric circular channels. FIGS. 4B–4F depict alternate embodiments in which the housing 12 has a shape that is different than the shape of the structure 16. Each of these embodiments may provide channels that remain open when the housing 12 or structure 16 is flexed. Some embodiments, such as 4D, may also provide improved surface area for heat transfer. In other exemplary embodiments, the inside cross-sectional shape of the housing 12 may differ from the outside cross-sectional shape. FIG. 4G depicts a further alternate embodiment in which structure 16 is replaced by structural elements of the housing that provide for separate channels, 18 and 20, when an energy delivery component 2 is inserted.

FIGS. 5–7 depict exemplary methods for performing treatment. As shown in FIG. 5, the energy delivery apparatus is assembled, as shown at step 502. The assembly may occur at a manufacturing site or in an operating room just prior to insertion in a patient. This assembly may include insertion of an energy delivery component. The energy delivery component may be coupled to an energy source. The energy delivery apparatus may also be coupled to a heat transfer medium supply. The assembly may occur prior to insertion of the apparatus in the tissue or during manufacturing of the apparatus. The apparatus may be inserted into the tissue, as shown at step 504.

FIG. 6 depicts an exemplary treatment method. The energy delivery apparatus is located proximate to the tissue to be treated, as shown at step 602. For example, the tissue may be a tumor and the distal end of the energy delivery apparatus may be located within the tumor or around the tumor. In the exemplary embodiment shown in FIG. 2B, once the skull is accessed, the energy delivery apparatus may be inserted into the soft tissue of the brain without a guide or catheter. Alternately, for tough tissues, a guide or catheter may be utilized. Heat transfer medium, such as a coolant, may be provided to the integrated energy delivery apparatus, as shown at step 604. Energy may be provided to an energy delivery component for delivery to the tissue, as shown at step 606. In one exemplary embodiment, a radial diffusive tip may be located within the tumor and may be used to disperse photons in a 360 degree pattern. In an alternate embodiment, an angular spread of photons may be provided to tissue using a directed tip located outside the tumor. The heat transfer medium may be provided in conjunction with the energy.

FIG. 7 depicts another exemplary treatment method. The energy delivery apparatus receives a heat transfer medium, as shown at step 702. The heat transfer medium may, for example, be a room-temperature saline coolant. Alternately, the heat transfer medium may be heated. The heat transfer medium may pass through the two channels of the integrated energy delivery apparatus. The heat transfer medium is then provided from the energy delivery apparatus, as shown in step 704. The heat transfer medium may be recirculated or sent to a waste recepticle. Energy may be received by the energy delivery apparatus, as shown in step 706. The energy may be received concurrently with the heat transfer medium.

In one exemplary embodiment, a cooled laser applicator in accord with the disclosure was constructed to house a fiberoptic energy delivery component having a diffusing tip, a 400 μm fiberotic core, and a 700 μm outer diameter and to allow circulation of room-temperature cooling fluid at a rate of approximately 15 mL/minute. The cooled laser applicator and internal fiberoptic were used in conjunction with a 980 nm wavelength laser energy source to produce thermal lesions in volumes of beef myocardium. For comparison, an identical diffusing tip fiberoptic laser applicator was also used without a cooling apparatus.

Using un-cooled diffusing tips, power levels of 6 and 7 W resulted in failure (burning) of the tip before the end of a 5-minute dose period. At 8 W, fiber failure was immediate. In contrast, no failures were observed using the cooled diffusing applicator at powers up to 10 W for up to 8 minutes. Further, while significant char resulted in two of the un-cooled lesions, only the largest water-cooled dose resulted in char formation, which was minimal and not in contact with the applicator. Lesion dimensions increased with dose, but for un-cooled fibers, did not increase with power due to premature tip failure. In the cooled case, lesion dimensions increased monotonically with dose.

While the above exemplary embodiments depict a cooling system and cooling medium, a heating system and heating medium may alternately be used. In general, a heat transfer medium may be used as fluid transferred through the channels.

Aspects of the disclosure are found in an integrated apparatus for delivering energy to a tissue. The integrated apparatus includes a housing having a distal end and a tubular structure located within the housing forming a first annulus between the tubular structure and the housing. The tubular structure is configured to accept an energy delivery component and is configured to form a second annulus between the tubular structure and the energy delivery component. The first annulus and the second annulus are configured to communicate with each other proximate to the distal end of the housing.

Further aspects of the disclosure are found in an integrated apparatus for delivering energy to a tissue. The integrated apparatus includes a housing having a distal end, a coupling assembly, and a tubular structure. The coupling assembly interfaces with the housing opposite the distal end. The coupling assembly includes a first fluid access port and a second fluid access port. The first fluid access port is associated with a first annulus and the second fluid access port is associated with a second annulus. The coupling assembly includes an opening for introducing an energy delivery component. The tubular structure is located within the housing, forming the first annulus between the tubular structure and the housing. The tubular structure is configured to form the second annulus between the tubular structure and the energy delivery component. The first annulus and the second annulus are configured to communicate with each other proximate to the distal end of the housing.

Additional aspects of the disclosure are found in an energy delivery system. The energy delivery system includes an energy source, a heat transfer fluid source and an integrated apparatus. The integrated apparatus includes a housing having a distal end and a tubular structure located within the housing forming a first annulus between the tubular structure and the housing. The tubular structure is configured to accept an energy delivery component and is configured to form a second annulus between the tubular structure and the energy delivery component. The first annulus and the second annulus are configured to communicate with each other proximate to the distal end of the housing.

Additional aspects of the disclosure are found in an integrated apparatus. The integrated apparatus includes a housing having a distal end having a penetrating portion. The housing is configured to accept a waveguide internal to the housing. The housing includes a first channel and a second channel internal to the housing. The first channel and the second channel are configured to communicate with each other proximate to the distal end and isolated from each other proximate to an end opposite the distal end.

Further aspects of the disclosure are found in an integrated apparatus for delivering energy to a tissue. The integrated apparatus includes a housing having an energy delivery end, a first channel portion located internal to the housing and configured to direct coolant flow toward the energy delivery end, and a second channel portion located internal to the housing and configured to direct coolant flow away from the energy delivery end.

Aspects of the disclosure are also found in a method of interstitial thermal therapy. The method includes receiving a heat transfer medium at an intake portion of an integrated energy delivery apparatus from a source external to the integrated energy delivery apparatus; providing the heat transfer medium from an output region of the integrated energy delivery apparatus to a destination external to the integrated energy delivery apparatus; and receiving energy at a proximal end of an energy delivery component. The energy delivery component has a distal end internal to the integrated energy delivery apparatus and terminates proximate to a distal end of the integrated energy delivery apparatus.

Further aspects of the disclosure are found in a method for delivering energy to a tissue. The method includes locating an integrated apparatus proximate to the tissue; providing transfer fluid via the first annulus and the second annulus to exchange heat with the energy delivery apparatus; and providing energy to the tissue via the energy delivery component. The integrated apparatus includes a housing having a distal end and a tubular structure located within the housing forming a first annulus between the tubular structure and the housing. The tubular structure is configured to accept an energy delivery component and is configured to form a second annulus between the tubular structure and the energy delivery component. The first annulus and the second annulus are configured to communicate with each other proximate to the distal end of the housing.

Additional aspects of the disclosure are found in a method of performing interstitial thermal therapy. The method includes inserting an integrated energy delivery apparatus into a tissue and delivering energy via a energy delivery component to the tissue. The integrated energy delivery apparatus includes a housing including a first fluid channel internal to the housing and a second fluid channel internal to the housing. The housing is configured to accept an energy delivery component internal to the housing.

Aspects of the disclosure are also found in a method of interstitial thermal therapy. The method includes assembling an integrated energy delivery apparatus and providing the integrated energy delivery apparatus for insertion into a tissue. The integrated energy delivery apparatus includes a housing including a first fluid channel internal to the housing and a second fluid channel internal to the housing. The housing is configured to accept an energy delivery component internal to the housing.

Further aspects of the disclosure are found in an energy delivery apparatus having an outside diameter less than 1.5 mm.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An integrated apparatus for delivering energy to a tissue, the integrated apparatus comprising:
   a housing having a distal end; and
   a tubular structure located within the housing forming a first annulus between the tubular structure and the housing, the tubular structure configured to accept an energy delivery component and configured to form a second annulus between the tubular structure and the energy delivery component, the first annulus and the second annulus configured to communicate with each other proximate to the distal end of the housing, wherein the first annulus and the second annulus have a respective first and second cross-sectional area proximate to the distal end and a respective third and fourth cross-sectional area away from the distal end wherein the third and fourth cross-sectional areas are larger than the first and second cross-sectional areas, respectively.

2. The integrated apparatus of claim 1, wherein a heat transfer fluid flows through the first annulus and the second annulus.

3. The integrated apparatus of claim 2, wherein the heat transfer fluid flows in a first direction through the first annulus and flows in an opposite direction through the second annulus.

4. The integrated apparatus of claim 1, wherein the housing has a penetrating portion proximate to the distal end.

5. The integrated apparatus of claim 1, wherein the energy delivery component comprises a waveguide.

6. The integrated apparatus of claim 1, wherein the energy delivery component comprises an optical fiber.

7. The integrated apparatus of claim 1, wherein the housing is flexible.

8. The integrated apparatus of claim 1, wherein the housing is substantially transparent to a range of radiation wavelengths.

9. The integrated apparatus of claim 1, wherein at least a portion of the housing is radio opaque.

10. The integrated apparatus of claim 1, wherein the housing comprises a polymer material.

11. The integrated apparatus of claim 10, wherein the polymer material is selected from the group consisting of polycarbonate, polyurethane, polyethylene, polypropylene, silicone, nylon, PVC, PET, PTFE, ABS, PES, PEEK, FEP, and combinations thereof.

12. The integrated apparatus of claim 1, wherein the first annulus and the second annulus are isolated from each other at an end opposite the distal end.

13. The integrated apparatus of claim 1, wherein the energy delivery component terminates in a diffusing tip proximate to the distal end of the housing.

14. The integrated apparatus of claim 1, wherein the housing includes a region of light scattering particles located proximate to the distal end of the housing.

15. The integrated apparatus of claim 1, wherein the housing includes a reflective component within the distal end.

16. The integrated apparatus of claim 1, wherein the housing includes at least one perforation connected to at least one of the first annulus and the second annulus.

17. The integrated apparatus of claim 16, wherein the at least one perforation is configured to alter the temperature of a tissue through fluid transfer between the interior of the housing and the exterior of the housing.

18. The integrated apparatus of claim 16, wherein an agent is delivered to a tissue via the at least one perforation.

19. The integrated apparatus of claim 18, wherein the agent is selected from the group consisting of anesthetics, therapeutic drugs, light absorptive agents, agents that alter the optical properties of the tissue, and sealants.

20. The integrated apparatus of claim 1, wherein the housing includes a fluid pathway located proximate to the distal end, the fluid pathway providing communication between a region exterior to the housing and hollow space that incorporates the first annulus and the second annulus.

21. The integrated apparatus of claim 20, wherein the fluid pathway is selectively opened and closed via translation of the energy delivery component.

22. The integrated apparatus of claim 1, wherein the housing comprises an external coating.

23. The integrated apparatus of claim 22, wherein the external coating comprises a non-stick coating.

24. The integrated apparatus of claim 22, wherein the external coating comprises a fluorinated polymer.

25. The integrated apparatus of claim 1, further comprising a coupling assembly to interface with the housing opposite the distal end.

26. The integrated apparatus of claim 25, wherein the coupling assembly comprises a first fluid access port and a second fluid access port, the first fluid access port configured to communicate with the first annulus and the second fluid access port configured to communicate with the second annulus.

27. The integrated apparatus of claim 26, wherein the coupling assembly comprises a seal to limit fluid transfer between the first fluid access port and the second fluid access port to flow through the first annulus and the second annulus.

28. The integrated apparatus of claim 25, wherein the coupling assembly comprises an opening for introducing the energy delivery component.

29. The integrated apparatus of claim 1, wherein the energy delivery component is configured to provide electromagnetic energy to a tissue within a patient.

30. The integrated apparatus of claim 29, wherein the electromagnetic energy facilitates necrosis of the tissue.

31. The integrated apparatus of claim 1, further comprising a plurality of spacers in at least one of the first annulus and the second annulus.

32. The integrated apparatus of claim 1, further comprising a reflective material located around a semi-circular section of the distal end of the housing.

33. The integrated apparatus of claim 32, where the reflective material is configured to permit energy emission over an angular region.

34. An integrated apparatus for delivering energy to a tissue, the integrated apparatus comprising:
a housing having a distal end;
a coupling assembly to interface with the housing opposite the distal end, the coupling assembly comprising a first fluid access port and a second fluid access port, the first fluid access port associated with a first annulus and the second fluid access port associated with a second annulus, the coupling assembly comprising an opening for introducing an energy delivery component; and
a tubular structure located within the housing forming the first annulus between the tubular structure and the housing, the tubular structure configured to form the second annulus between the tubular structure and the energy delivery component, the first annulus and the second annulus configured to communicate with each other proximate to the distal end of the housing, wherein the first annulus and the second annulus have a respective first and second cross-sectional area proximate to the distal end and a respective third and fourth cross-sectional area away from the distal end wherein the third and fourth cross-sectional areas are larger than the first and second cross-sectional areas, respectively.

35. The integrated apparatus of claim 34, wherein a heat transfer fluid flows through the first annulus and the second annulus.

36. The integrated apparatus of claim 35, wherein the heat transfer fluid flows in a first direction through the first annulus and flows in an opposite direction through the second annulus.

37. The integrated apparatus of claim 34, wherein the housing has a penetrating portion proximate to the distal end.

38. The integrated apparatus of claim 34, wherein the energy delivery component comprises a waveguide.

39. An energy delivery system comprising
an energy source;
a heat transfer fluid source; and
an integrated apparatus comprising:
a housing having a distal end; and
a tubular structure located within the housing forming a first annulus between the tubular structure and the housing, the tubular structure configured to accept an energy delivery component and configured to form a second annulus between the tubular structure and the energy delivery component the first annulus and the second annulus configured to communicate with each other proximate to the distal end of the housing, wherein the first annulus and the second annulus have a respective first and second cross-sectional area proximate to the distal end and a respective third and fourth cross-sectional area away from the distal end wherein the third and fourth cross-sectional areas are larger than the first and second cross-sectional areas, respectively.

40. The energy delivery system of claim 39, wherein a heat transfer fluid flows through the first annulus and the second annulus.

41. The energy delivery system of claim 40, wherein the heat transfer fluid flows in a first direction through the first annulus and flows in an opposite direction through the second annulus.

42. The energy delivery system of claim 39, wherein the housing has a penetrating portion proximate to the distal end.

43. An integrated apparatus comprising:
a housing having a distal end having a penetrating portion, the housing configured to accept a waveguide internal to the housing, the housing including:
a first channel and a second channel internal to the housing, the first channel and the second channel configured to communicate with each other proximate to the distal end and isolated from each other proximate to an end opposite the distal end;

wherein the first channel and the second channel have a respective first and second cross-sectional area proximate to the distal end and a respective third and fourth cross-sectional area away from the distal end wherein the third and fourth cross-sectional areas are larger than the first and second cross-sectional areas, respectively.

44. The integrated apparatus of claim 43, wherein a heat transfer fluid flows through the first channel and the second channel.

45. The integrated apparatus of claim 44, wherein the heat transfer fluid flows in a first direction through the first channel and flows in an opposite direction through the second channel.

46. An integrated apparatus for delivering energy to a tissue, the integrated apparatus comprising:
    a housing having an energy delivery end;
    a first channel portion located internal to the housing and configured to direct coolant flow toward the energy delivery end; and
    a second channel portion located internal to the housing and configured to direct coolant flow away from the energy delivery end; and
    wherein the first channel and the second channel have a respective first and second cross-sectional area proximate to the distal end and a respective third and fourth cross-sectional area away from the distal end wherein the third and fourth cross-sectional areas are larger than the first and second cross-sectional areas, respectively.

47. The integrated apparatus of claim 46, further comprising an energy delivery component located internal to the housing.

48. The integrated apparatus of claim 46, wherein a heat transfer fluid flows through the first channel portion and the second channel portion.

49. The integrated apparatus of claim 48, wherein the heat transfer fluid flows in a first direction through the first channel potion and flaws in an opposite direction through the second channel portion.

* * * * *

UNITED STATES PATENT AND TRADEMARK OFFICE
CERTIFICATE OF CORRECTION

PATENT NO.       : 7,270,656 B2
APPLICATION NO.  : 10/703304
DATED            : September 18, 2007
INVENTOR(S)      : Ashok Gowda et al.

It is certified that error appears in the above-identified patent and that said Letters Patent is hereby corrected as shown below:

Col. 14, Claim 39, Line 11, please delete "delivery component the first" and insert therefor --delivery component, the first--.

Col. 16, Claim 49, Line 3, please delete "potion and flaws" and insert therefor --portion and flows--.

Signed and Sealed this

Eighth Day of January, 2008

JON W. DUDAS
*Director of the United States Patent and Trademark Office*